United States Patent [19]

Bosslet et al.

[11] Patent Number: 5,621,002
[45] Date of Patent: Apr. 15, 1997

[54] PRODRUGS FOR ENZYME MEDIATED ACTIVATION

[75] Inventors: Klaus Bosslet; Jörg Czech, both of Marburg; Dieter Hoffmann, Marburg-Elnhausen, all of Germany; Andrea Vasella; Roland Hoos, both of Zürich, Switzerland; François Tillequin, Paris, France; Jean-Claude Florent, Les Ulis, France; Michel Azoulay; Claude Monneret, both of Paris, France; Jean-Claude Jacquesy, Buxerolles, France; Jean-Pierre Gesson, Chansseneuil du Poitou, France; Michel Koch, La Celle Saint Cloud, France

[73] Assignees: Behringwerke Aktiengesellschaft, Marburg, Germany; Laboratoires Hoechst S/A, Paris La Défense, France

[21] Appl. No.: 302,459

[22] Filed: Sep. 9, 1994

[30] Foreign Application Priority Data

Sep. 9, 1993 [EP] European Pat. Off. ............ 93114475

[51] Int. Cl.$^6$ .................... A61K 31/335; A61K 31/34
[52] U.S. Cl. .................... 514/451; 514/461; 435/188.5
[58] Field of Search .................... 514/478, 479, 514/480, 451, 461; 435/188.5; 424/130.4

[56] References Cited

FOREIGN PATENT DOCUMENTS

| | | |
|---|---|---|
| 2109304 | 10/1992 | Canada. |
| 0441218A3 | 8/1991 | European Pat. Off.. |
| 0501215A3 | 9/1992 | European Pat. Off.. |
| 0511917A1 | 11/1992 | European Pat. Off.. |
| 0540859A1 | 5/1993 | European Pat. Off.. |
| 2212014 | 10/1972 | Germany. |
| WO81/01145 | 4/1981 | WIPO. |
| WO90/03188 | 4/1990 | WIPO. |

OTHER PUBLICATIONS

T. A. Connors, "Prodrugs in cancer chemotherapy," *Xenobiotica*, 1986, vol. 16, Nos. 10/11, pp. 975–988.

G.W. Philpott et al., "Selective Cytotoxicity of Hapten–Substituted Cells With An Antibody–Enzyme Conjugate," *The Journal of Immunology*, 1973, vol. 111, pp. 921–929.

K.D. Bagshawe et al., "A cytotoxic agent can be generated selectively at cancer sites," *Br. J. Cancer*, 1988, vol. 58, pp. 700–703.

P.D. Senter et al., "Generation of Cytotoxic Agents by Targeted Enzymes," *Bioconjugate Chem.*, 1993, vol. 4, pp. 3–9.

K. Bosslet et al., "Molecular and functional characterisation of a fusion protein suited for tumour specific prodrug activation," *Br. J. Cancer*, 1992, vol. 65, pp. 234–238.

S.C. Goshorn et al., "Genetic Construction, Expression, and Characterization of a Single Chain Anti–Carcinoma Antibody Fused to B–Lactamase," *Cancer Research*, 1993, vol. 53, pp. 2123–2127.

K.D. Bagshawe et al., "Antibody Directed Enzyme Prodrug Therapy (Adept): Clinical Report," *Disease Markers*, 1991, vol. 9, pp. 233–238.

K.M. Munir et al., "Thymidine kinase mutants obtained by random sequence selection," *Proc. Natl. Acad. Sci. USA*, 1993, vol. 90, pp. 4012–4016.

*Primary Examiner*—Charles L. Patterson, Jr.
*Attorney, Agent, or Firm*—Finnegan, Henderson, Farabow, Garrett & Dunner, L.L.P.

[57] ABSTRACT

Enzymatically clearable prodrugs with reduced Michaelis-Menten constant (Km) are described.

9 Claims, No Drawings

PRODRUGS FOR ENZYME MEDIATED ACTIVATION

This invention refers to enzymatically cleavable prodrugs with reduced Michaelis-Menten constant (Km).

A prodrug may be defined as a chemical which is non-toxic and pharmacodynamically inert, but which can be transformed in vivo to a pharmacologically active drug.

The invention refers to the field of drug-targeting, which deals with site-specific delivery of drugs in vivo. Site-specific delivery preferably increases the selectivity of drugs and reduces their undesirable side effects.

One potential approach to achieve a site-specific delivery consists in applying untoxic prodrugs which can be site-specifically activated to cytotoxic drugs using prelocalized prodrug cleaving catalysts like enzymes, muteins derived from enzymes, catalytic antibodies, antibody enzyme conjugates or fusion proteins.

This approach combines the advantage of drug delivery via prodrugs (i.e. increased stability, adjusted solubility, improved route of administration, more favourable distribution, improved pharmacokinetics, by-passing resistance; T. A. Connors, Xenobiotica 16, 975–988, 1986) with the preferential tumour specific activation mediated by a catalytic principle. The use of exogenous enzymes or polyclonal antibody enzyme conjugates for prodrug activation was pioneered by Graffi (Deutsche Offenlegungsschrift 22 12 014), and Philpott et al. (J. Immunol. 111, 921, 1973).

More recently the original teaching from Graffi and Philpott was exemplified and improved by the use of monoclonal antibody enzyme conjugates as prodrug activating catalysts (Bagshawe et al., Brit. J. Cancer, 58, 700, 1988; Senter et al., Bioconjugate Chem. 4, 3–9, 1993) or fusion proteins (Bosslet et al., Brit. J. Cancer, 65, 234–238, 1992; Goshorn et al., cancer Res. 53, 2123–2127, 1993).

Despite these improvements, the systems described so far have some major disadvantages for clinical applications:

a) monoclonal antibody enzyme conjugates produced by chemical coupling have as a major drawback a strong immunogenicity in man due to the xenogenic origin of the antibody moiety and the enzyme (Bagshawe et al., Disease Markers 9: 233–238, 1991). As a consequence of this high immunogenicity repetitive applications in man are possible only to a very limited extent;

b) fusion proteins consisting of non-humanised binding moieties and xenogenic enzymes produced by recombinant DNA technology will be immunogenic in man as well with disadvantages comparable to monoclonal antibody enzyme conjugates, if repetitive applications are needed;

c) fusion proteins consisting of humanised binding moieties and human enzymes will probably not be very immunogenic in man most probably allowing repetitive treatment cycles in man. Nevertheless, the two major disadvantages of human fusion proteins are the possibly lower turnover rate (Vmax) of the human enzyme moiety as well as the possibly higher prodrug (substrate) concentration needed to obtain significant catalysis in comparison to xenogenic enzymes having a high turnover rate and a low Michaelis-Menten constant (Km).

This limitation of human fusion proteins (low Vmax and high Km) given by the intrinsic nature of the human enzyme moiety can be overcome by state of the art methodology only to a very limited extent (factor 4) by random mutagenesis in the active site of the enzyme (Munir et al., PNAS U.S.A. 90:4012–4016, 1993).

Surprisingly, it has been found that the limitation by a high Km, an intrinsic property of most human enzymes applicable for in vivo prodrug activation, can be overcome by novel prodrugs.

These prodrugs have the formula I, $$S-Z-W \qquad (I)$$

wherein W means a pharmacologically active substance, Z stands for a self-immolative spacer or a bond and S is a moiety such that the S—Z bond is enzymatically cleaved at an at least 2-fold lower Michaelis-Menten Constant compared to the natural enzyme substrate.

The prodrugs of the invention have the common characteristic to be cleaved by enzymes at significantly lower molar prodrug concentration as the natural or standard substrates used for enzymatic analysis or appropriate state of the art prodrugs (WO 92/19639). They are therefore named Km-reduced prodrugs.

The prodrugs of the invention have as another common characteristic a modified competitive enzyme activity inhibitor (S) as a crucial structural component which can be linked directly or via a spacer moiety (Z) to the pharmacologically active substance (W). Preferably the spacer is self-immolative generating the pharmacologically active substance after enzymatic cleavage of the S—Z bond. A self-immolative spacer is defined as a moiety which is bound through two bonds to two molecules and which eliminates itself from the second molecule if the bond to the first molecule is cleaved.

The preferred Km-reduced prodrugs are substrates for human glycosidases and have the general formula II:

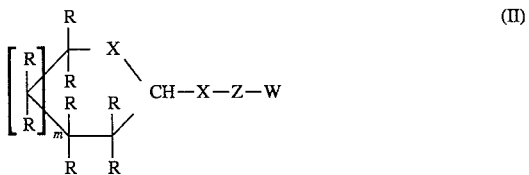

wherein

R may be independent from each other H, OH, F, $NH_2$, COOH, $CH_2$—COOH, CHOH—COOH, $PO_3H_2$, $CH_2$—$PO_3H_2$ or CHOH—$PO_3H_2$, X may be NH, O or S, m may be 0 or 1, Z stands for a self-immolative spacer or a bond and W means a pharmacologically active substance.

Not included are β-D-glucuronide-Z-anthracyclin compounds:

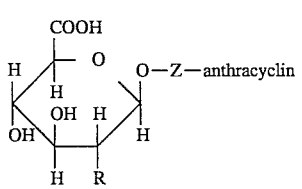

with R = OH, $NH_2$.

Especially preferred are Km-reduced prodrugs which are substrates for β-glucuronidase and have the general formula III:

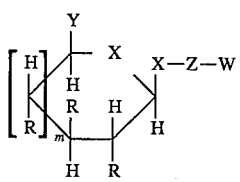 (III)

wherein

Y may be COOH, CH₂—COOH, CHOH—COOH, PO₃H₂, CH₂PO₃H₂ or CHOH—PO₃H₂,

X may be NH, O or S,

R may be independent from each other F, NH₂, H or OH, m may be 0 or 1,

Z stands for a bond or a self-immolative spacer preferentially a moiety with the formula

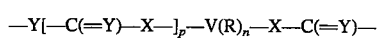

wherein

V is an aromate or a hetero aromate or an aliphate with conjugated double bonds or an amino acid residue which cycles after cleavage of the glycosyl residue, preferentially with 5–20 carbon atoms and 0–4 hereto atoms, wherein hetero atom means N, O or S, substituted with R being independently from each other H, methyl, methoxy, carboxy, methyloxycarbonyl, CN, hydroxy, nitro, fluor, chlor, brom, sulfonyl, sulfonamid or sulfon (C$_{1-4}$)-alkylamid and p 0 or 1 n an integer of 0 to 25, preferentially 1 or 2

X O, NH, methylenoxy, ,methylenamino or methylen (C$_{1-4}$)-alkylamino,

Y O or NH and

W means a pharmacologically active substance preferentially an anthracycline such as doxorubicin, 4'-epi-doxorubicin, 4- or 4'-desoxy-doxorubicin, or an etoposide, N-bis-(2-chlorethyl)-4-hydroxyaniline, 4-hydroxycyclophosphamide, vindesine, vinblastine, vincristine, terfenadine, terbutaline, fenoterol, salbutamol, muscarine, oxyphenbutazone, salicylic acid, p-aminosalicylic acid, 5-fluorouracil, 5-fluorocytidine, 5-fluorouridine, methotrexate, diclofenac, flufenamicacid, 4-methylaminophenazone, theophylline, nifedipine, mitomycine C, mitoxantrone, camptothecine, m-AMSA, taxol, nocodaxol, colchicine, cyclophosphamide, rachelmycin, cisplatin, melphalan, bleomycin, nitrogen-mustard, phosphoramide-mustard, quercetin, genistein, erbstatin, tyrphostin, rohitukine-derivative ((–)-cis-5,7-dihydroxy-2-(2-chlorphenyl)-8-[4-(3-hydroxy-1-methyl)-piperidinyl]-4H-1-benzopyran-4-on; EP 89119710.5), retinoic acid, burytic acid, phorbol ester, DMSO, aclacinomycin, progesterone, buserelin, tamoxifen, mifepristone, onapristone, N-(4-aminobutyl)-5-chloro-2-naphtalen-sulfonamide, pyridinyloxazol-2-one, quinolyl-, isoquinolyloxazolone-2-one, staurosporine, ethanolamine, verapamil, forskolin, 1,9-dideoxyforskolin, quinine, quinidine, resetpine, 18-O-(3,5-dimethoxy-4-hydroxybenzoyl)-reserpate, lonidamine, buthionine sulfoximine, diethyldithiocarbamate, cyclosporine A, azathioprine, chlorambucil, N-(4-tri-fluormethyl)-phenyl-2-cyano-3-hydroxy-croton-acid-amide (WO 91/17748), 15-deoxyspergualin, FK 506, ibuprofen, indomethacin, aspirin, sulfasalazine, penicillamine, chloroquine, dexamethasone, prednisolone, lidocaine, propafenone, procaine, mefonamic acid, paracetamol, 4-aminophenazone, muskosine, orciprenaline, isoprenaline, amiloride, p-nitrophenylguanidinobenzoat or their derivatives additionly substituted with one or more hydroxy-, amino- or iminogroups, linked through a hydroxy-, amino- or imino group to Z.

Not included are β-D-glucuronide-Z-anthracyclin compounds:

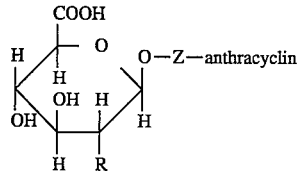 with R = OH, NH₂.

Enzyme in this application may also mean a catalytic antibody. The compounds described herein can be prepared by prior art methods.

Km-reduced prodrugs, selective for human β-glucuronidase, are described in the following sections. Prodrug A (example 1) may be looked upon as derived from the competitive β-glucuronidase inhibitor saccharolactone:

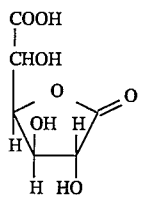

EXAMPLE 1

Prodrug A, B, C:

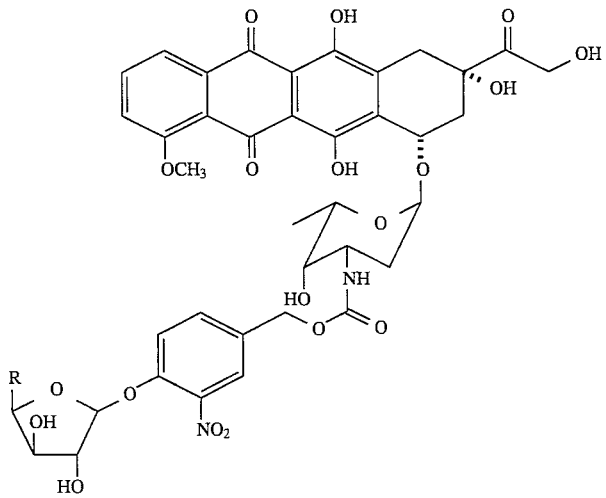

Prodrug A: R=CHOH—COOH
Prodrug B: R=CH₂—COOH
Prodrug C: R=COOH

Experimental procedure for prodrug A:
Preparation of 1,2,5-tri-O-acetyl-aldehydo-D-glucurono-3,6-lactone (compound 7).

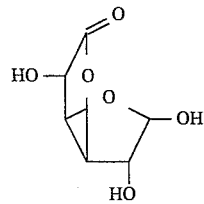

Compound 5

3,6-Glucarolactone (Compound 5) (45 g) was slowly added to a cooled (0°–5° C.) mixture of dry pyridine (225 ml) and Ac₂O (185 ml). The internal temperature was maintained at 5° C. during the addition and after all the lactone has been dissolved, the reaction mixture was allowed to be stirred for additional 2 hours. The colourless solution was then poured into 3 liters of a mixture of water and crushed ice and vigorously stirred for approximately 3 hours. The precipitate was collected and washed with water, and after drying a solid was isolated which contains 70 g of a mixture of α and β tri-O-acetyl-glucuronolactone (compound 7). This mixture was directly used for the next step.
Preparation of 2,5-di-O-acetyl-α-D-glucurono-3,6-lactone-α-furanosyl bromide (compound 8).

Titanium bromide (16.6 g, 45 mmol) as added to a stirred solution of compound 7 (70 g, 23.3 mmol) in dichloromethane (200 ml) maintained in the dark and under nitrogen atmosphere. After stirring overnight, additional TiBr₄ was added (8.3, 22 mmol). After 24 additional hours, the reaction mixture was diluted with dichloromethane (150 ml) and the organic solution poured into crushed ice water. The organic layer was separated, washed with water, dried and evaporated under reduced pressure. This gave compound 8 (65 g) pure enough for the next step.
Preparation of (2-nitro-4-formylphenyl)-2,5-di-O-acetyl-β-D-glucurono-3,6-lactone furanoside (compound 9).

It was prepared from compound 8 (15 g, 50 mmol) and from 4-hydroxy-3-nitrobenzaldehyde according to the procedure already described in WO 92/19639. This afforded 12 g (61.6%) of compound 9.
Preparation of (2-nitro-4-formylphenyl)-2,3,5-tri-O-acetyl-β-D-glucuronate (compound 1a).

To a solution of solid sodium hydroxide (50 mg) in methanol (125 ml), compound 9 (10 g) was added. The solution was stirred at room temperature for 4 h and evaporated under reduced pressure. This resulted in a crude mixture which was immediately dissolved in anhydrous pyridine (50 ml). After cooling to 0° C., acetic anhydride (40 ml) was added and the reaction mixture was subsequently stirred for additional 18 h. Extraction with dichloromethane followed by usual work-up resulted in 6.6 g of compound 1a (65 % overall yield).
Preparation of (2-nitro-4-hydroxymethylphenyl)-2,3,5-tri-O-acetyl-β-D-glucuronate (compound 2a).

It was prepared by sodium borohydride reduction of compound 1a (6 g) according to the procedure already described in the WO 92/19639. This yielded 5.6 g (95%) of compound 2a.
Preparation of 4-(2,3,5-tri-O-acetyl-β-D-methylglucuronofuranosyl)-3-nitro-p-nitrobenzyloxycarbonate (compound 3a).

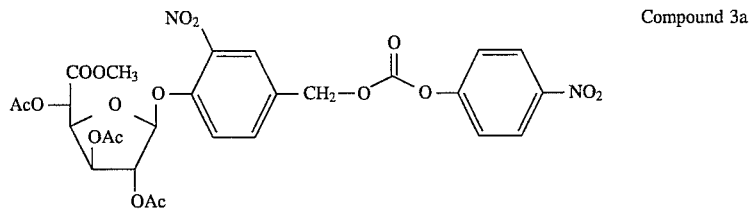

Compound 3a

It was prepared coupling of compound 2a (6 g) with 4-nitrophenyl chloroformiate (yield 75%) according to the procedure already described in the WO 92/19639.
Preparation of prodrug A:

Prodrug A was prepared from compound 3a and doxorubicin (yield 83%) followed by treatment with sodium methoxide in methanol and then sodium hydroxide.

EXAMPLE 2

Preparation of 4-methylumbelliferyl(5R)-5-phosphonyl-β-D-xylopyranoside (16):

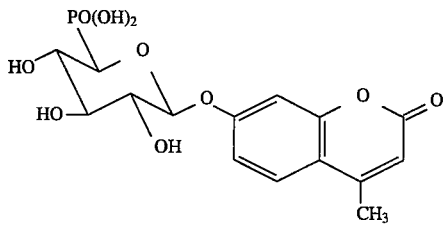

Allyl 6-O-trityl-α-D-glucopyranoside (2). A solution of allyl α-D-glucopyranoside (1) (prepared according to R. E. Wing, J. N. BeMiller, Carbohydr. Res. 1969, 10, 441) (12.5 g, 56.8 mmol) and triphenylmethyl chloride (20.0 g, 71.7 mmol) in dry pyridine (120 ml) was stirred at r.t. for 12 h, and at 60° for 1 h. After the addition of triphenylmethyl chloride (12.0 g, 43.0 mmol), the solution was stirred at 60° until all starting material has disappeared (3–4 h). $H_2O$ (120 ml) was added to the still warm solution. Extraction with EtOAc, extraction of the combined org. layers with 1M aq. $H_2SO_4$ and brine, evaporation of the organic layer and FC (400 g $SiO_2$, toluene/actone 2:1→toluene/acetone 1:1) gave 23.3 g (90%) of 2. Grey glassy solid.

Allyl 2,3,4-tri-O-benzyl-6-O-trityl-α-D-glucopyranoside (3). A solution of 2 (15.9 g, 34.3 mmol) in dry THF (390 ml) was treated with a suspension of NaH (6.9 g, ca. 150 mmol) at r.t. for 10 min. BnBr (25.0 ml, 211 mmol) and $Bu_4NI$ (1.9 g, 5.1 mmol) were added. The solution was heated under reflux until TLC indicated completion of the reaction (ca. 12 h). $Et_2O$ was added, and the solution was filtered through silica. The filtrate was evaporated, and the residue was subjected to FC (600 g $SiO_2$, $Et_2O$/hexane 1:9→$Et_2O$) to give 21.4 g (85%) of 3. $R_f$ (EtOAc/hexane 1:4) 0.36. $^{13}$C-NMR (75 MHz, $C_6D_6$): 63.46 t); 68.49 (t); 71.33 (d); 72.96 (t); 75.12 (t); 75.74 (t); 78.93 (d); 81.40 (d); 82.85 (d); 86.95 (s); 96.44 (d); 117.21 (t); 127.29–129.32 (several d); 134.73 (d); 139.11 (s); 139.32 (s); 139.89 (s); 144.78 (s, triple intensity).

Allyl 2,3,4-tri-O-benzyl-α-D-glucopyranoside (4). A solution of $BF_3.OEt_2$ (5.0 ml, 39.8 mmol) in MeCN (90 ml) was added dropwise to a cooled (0°) solution of 3 (13.4 g, 18.3 mmol) and $Et_3SiH$ (14.5 ml, 91.5 mmol) in dry $CH_2Cl_2$ (150 ml). After 10 min., a sat. aq. solution of $NaHCO_3$ (100 ml) and $H_2O$ (200 ml) were added. The mixture was shaken vigorously, the aq. layer was extracted with $CH_2Cl_2$, the combined organic layers were extracted with brine, dried ($MgSO_4$), and evaporated. FC (400 g $SiO_2$, EtOAc/hexane 1:5→EtOAc/hexane 1:1) afforded 8.35 g (93%) of 4. $R_f$ (EtOAc/hexane 1:2) 0.20.

Allyl 2,3,4-tri-O-benzyl-α-D-glucopyranuronide tert.-butyl ester (5). A solution of 4 (8.35 g, 17.0 mmol) in DMF/$CH_2Cl_2$ 4:1 (45 ml) was added to a solution of $CrO_3$ (6.8 g, 6.8 mmol) in DMF/$CH_2Cl_2$ 4:1 (180 ml) and pyridine (11.0 ml, 142 mmol). which had been stirred vigorously for 30 min r.t. After addition of $Ac_2O$ (13.0 ml, 11 8 mmol) and tert -BuOH (34.0 ml, 362 mmol), the solution was stirred for 9 h at r.t., before MeOH (30 ml) was added. After 30 min., the mixture was concentrated to one quarter of its volume and diluted with $Et_2O$ (250 ml). Filtration through $Na_2SO_4$ and $SiO_2$ (300 g), elution with $Et_2O$, evaporation and FC (330 g $SiO_2$, AcOEt/hexane 1:9) afforded 6.30 g (66%) of 5. $R_f$ (EtOAc/hexane 1:2) 0.63. $^{13}$C-NMR (50 MHz, $CDCl_3$): 27.94 (q, triple intensity); 68.69 (t) ; 71.44 (d); 73.43 (t); 75.89 (t), 79.51 (d); 79.73 (d); 81.45 (d); 82.12 (s); 96.78 (d); 118.83 (t); 127.66–128.50 (several d); 133.56 (d); 138.06 (s); 138.21 (s); 138.69 (s); 16.8.84 (s).

Allyl 2,3,4-tri-O-benzyl-α-D-glucopyranuronide (6). A solution of 5 (6 25 g, 11.1 mmol) in HCOOH (150 ml) was stirred at r.t. for 30 min. Evaporation yielded 5.60 g (99%) of chromatographically pure 6. $R_f$ (EtOAc/hexane/HCOOH 1:1:trace) 0.47. $^{13}$C-NMR (75 MHz, $CDCl_3$): 68.88 (t); 69.86 (d); 73.40 (t); 75.33 (t); 75.06 (t); 79.14 (d); 79.26 (d); 81.42 (d); 96.13 (d); 118.90 (t); 127.77–128.55 (several d); 133.18 (d); 137.47 (s); 137.84 (s), 138.46 (s); 174.18 (s).

Allyl(5R)-5-acetoxy-2,3,4-tri-O-benzyl-α-D-xylopyranoside (7). A stirred solution of 6 (5.60 g, 11.1 mmol) in $C_6H_6$ (50 ml) and pyridine (5 ml) was treated with $Pb(OAc)_4$ (16.80 g, ca. 32 mmol) under $N_2$ at 60° for 25 min. Filtration through $SiO_2$, elution with $Et_2O$, evaporation and FC (300 g $SiO_2$, AcOEt/hexane 1:6) afforded 4.1 g (71%) of 7. $R_f$ (EtOAc/hexane 1:4) 0.29. IR ($CHCl_3$): 3089w, 3067w, 3008w,. 2933w, 2874w, 1759s, 1497w, 1455w, 1367m, 1248w, 1161m, 1070s, 1028s, 937w. $^{13}$C-NMR (50 MHz, $CDCl_3$): 21.16 (q); 68.78 (t); 73.67 (t); 75.47 (t); 76.33 (t); 79.50 (d); 80.54 (d); 81.37 (d); 90.18 (d); 95,35 (d); 119.09 (t); 128.05–128.84 (several d); 133.68 (d); 138.36 (s); 138.63 (s); 139.01 (s), 169.75 (s).

Allyl(5S)-5-hydroxy-2,3,4-tri-O-benzyl-α-D-xylopyranoside (8). At −78°, DIBAH (2.8 ml of a 20% solution in toluene, ca. 2.9 mmol) was added dropwise to a solution of 7 (553 mg, 0.96 mmol) in $CH_2Cl_2$ (20 ml). After 15 min., a sat. solution of $NH_4Cl$ (2 ml) was added. The mixture was warmed up to r.t., diluted with $H_2O$ and a 1M solution of $H_2SO_4$ (10 ml). The aq. layer was extracted with $CH_2Cl_2$ (3×), the combined org. layers were extracted with brine (2×), dried ($MgSO_4$) and evaporated to yield 499 mg (98%) of crystalline 8 which was used without further purification in the next step. Rf (EtOAc/hexane 1:2) 0.32. $^1$H-NMR (300 MHz, $CDCl_3$): 2.92 (broad s, OH); 3.33 (dd, J=9.2, 7.8, H—C (4)); 3.60 (dd, J=9.7, 3.7, H—C (2)); 3.99 (t, J=9.5, H—C (3)); 4.07 (ddt, J=12.9, 6.6, 1.2, OAll); 4.23 (ddt, J=12.9, 5.2, 1.4, OAll); 4.65 (d, J=12.0), 4.79 (d, J=12.0, $PhCH_2$); 4.78 (d, J=3.7, H—C (1)); 4.81 (d, J=11.2), 4.89 (d, J=11.9, $PhCH_2$); 4.85 (d, J=10.9), 4.93 (d, J=10.9, $PhCH_2$); 5.06 (d, J=7.8, H—C (5)); 5.24 (dq, J=10.3, 1.5, OAll); 5.34 (dq, J=17.2, 1.5, OAll); 5.93 (dddd, J=17.1, 10.3, 6.6, 5.2, OAll); 7.28–7.42 (m, 15 arom. H).

Allyl(5S)-5-trichloracetimidyloxy-2,3,4-tri-O-benzyl-α-D-xylopyranoside (9). MTBD (66 μl, 0.46 mmol) was added to a cooled (−30°) solution of crude 8 (200 mg, ca. 0.42 mmol) and $Cl_3CCN$ (0.63 ml, 6.3 mmol) in dry $ClCH_2CH_2Cl$ (6 ml). After 10 min, the solution was filtered through $SiO_2$, the $SiO_2$ was eluted with $Et_2O$, and the combined filtrates were evaporated to give crude 9 which was sufficiently pure ($^1$H-NMR, TLC) to be used in the next step. $R_f$ (EtOAc/hexane 1:2) 0.53.

Allyl(5R)-5-dimethylphosphonyl-2,3,4-tri-O-benzyl-α-D-xylopyranoside (10) and allyl(5S)-5-dimethylphosphonyl-2,3,4-tri-O-benzyl-α-D-xylopyranoside (11). TMSOTf (83 μl, 0.46 mmol) was added to a cooled (−17°) solution of crude 9 (350 mg) and $P(OMe)_3$ (240 μl, 1.26 mmol) in dry MeCN (6 ml). The solution was warmed to 0°, kept at this temperature for 3 h, and filtered through SiO$_2$. The SiO$_2$ was eluted with Et$_2$O, and the combined flitrates were evaporated. The residue (396 mg) was subjected to FC (22 g SiO$_2$, EtOAc/hexane 1:1) to give a mixture of 10 and its (5S) isomer 11 (147 mg, 62% from 7). This mixture was further purified by HPLC (EtOAc/hexane 2:1) to give 49 mg (21% from 7) of 10 and 52 mg (22% from 7) of 11. Data of 10: R$_f$ (EtOAc/hexane 1:1) 0.12. $^1$H-NMR (500 MHz, CDCl$_3$): 3.55 (dd, J=9.6, 3.6, H—C (2)); 3.69 (d, J=10.8, OMe); 3.80 (d, J=10.5, OMe), 3.81 (dt, J=10.6, 8.8, H—C (4)); 3.99 (t, J=9.1, H-(3)); 4.00 (ddt, J=12.8, 6.6, 1.2 OAll); 4.05 (dd, J=10.5, 9.8, H—C (5)); 4.16 (ddt, J=12.8, 5.2, 1.4, OAll); 4.62 (d, J=12.1), 4.77 (d, J=12.1, PhCH$_2$); 4.80 (d, J=10.6), 4.89 (d, J=10.3 PhCH$_2$); 4.81 (d, J=4.7, H—C (2)); 4.83 (d, J=11.2), 4.97 (d, J=10.9, PhCH$_2$); 5.24 (dq, J=10.3, 1.1, OAll); 5.33 (dq, J=17.2, 1.6, OAll); 5.93 (dddd, J=17.1, 10.3, 6.7, 5.2, OAll); 7.24–7.35 (m, 15 arom. H). $^{13}$C-NMR (125 MHz, CDCl$_3$): 52.74 (dq, J(P,C)=6.8); 53.88 (dq, J(P,C)=6.5); 65.86 (dd, J(C,P)=175.1); 68.73 (t); 73.46 (t); 75.26 (t); 75.90 (t); 78.40 (dd, J(C,P)=2.7); 79.35 (dd, J(C,P)=1.0); 82.01 (dd, J(C,P)=17.9; 96.40 (dd, J(C,P)= 15.0); 118.66 (t); 127.63–128.49 (several d); 133.28 (d); 138.00 (s); 138.11 (s); 138.63 (s). $^{31}$P-NMR (203 MHz, CDCl$_3$): 24.60.

Prop-1-enyl(5R)-5-dimethylphosphonyl-2,3,4-tri-O-benzyl-α-D-xylopyranoside (12). A solution of activated 1,5-cyclooctadiene-bis[methyldiphenylphosphine]-iridium hexafluorophosphate (15 mg) in dry THF (5 ml) was added to a stirred solution of 10 (257 mg; 0.452 mmol) in dry THF (10 ml). After 2 h, TLC indicated completion of the reaction, and the solution was evaporated to give 57 mg of crude 12 which was used without purification in the next step. R$_f$ (EtOAc(hexane 3:1) 0.39.

(5R) -5-dimethylphosphonyl-2,3,4-tri-O-benzyl-α-D-xylopyranose (13). A stirred solution of crude 12 (57 mg) and yellow HgO (118 mg; 0.54 mmol) in H$_2$O/acetone 1:10 (10 ml) was treated with a solution of HgCl$_2$ (148 mg; 0.55 mmol) in H$_2$O/acetone 1:10 (5 ml). After completion of the reaction, Et$_2$O was added. The Et$_2$O layer was washed with a semisaturated solution of KI and with brine. SiO$_2$ (2 g) was added, the mixture was evaporated and subjected to FC (15 g SiO$_2$, EtOAc/hexane 3:1→ EtOAc/hexane 5:1) to give 216 mg (90% from 10) of 13. R$_f$ (EtOAc/hexane 3:1) 0.16.

O-[(5R)-5-dimethylphosphonyl-2,3,4-tri-O-benzyl-α-D-xylopyranoside]-trichloroacetimidate (14). At −30°, MTBD (1.1 Eq.) was added to a solution (0.05M) of 13 and Cl$_3$CCN (15 Eq.) in dry CH$_2$Cl$_2$. After completion of the reaction, the solution was filtered through SiO$_2$, the SiO$_2$ was eluated with Et$_2$O, and the combined eluants were evaporated to give crude 14 which was used without purification in the next step.

4-Methylumbelliferyl (5R)-5-dimethylphosphonyl-2,3,4-tri-O-benzyl-β-D-xylopyranoside (15). A solution of crude 14 (1 eq.) and 4-methylumbelliferone (2 Eq.) in dry MeCN (0.05M) at −20° was treated with BF$_3$OEt$_2$ (1 Eq.). After completion of the reaction, H$_2$O was added. The aq. phase was extracted with EtOAc (3×), the combined org. phases were washed with brine, dried over MgSO$_4$ and evaporated. The residue was subjected to FC to give 15.

4-Methylumbelliferyl (5R)-5-dimethylphosphonyl-β-D-xylopyranoside (16). A solution of 15 in MeOH (0.05M) was treated with H$_2$ in the presence of Pd/C 1:10 [K. Wallimann, Helv. Chim. Acta 1990, 73, 1359]. Filtration through Celite and evaporation gave crude 16 which was purified by FC (MeOH/EtOAc).

4-Methylumbelliferyl (5R)-5-phosphonyl-β-D-xylopyranoside (17). A solution of 16 in CH$_2$Cl$_2$ (0.05M) was treated under N$_2$ at 0° with Me$_3$SiBr (30 Eq.) [C. E. McKenna, Tetrahedron Lettr. 1977, 155]. After completion of the reaction, MeOH was added, the mixture concentrated i.v., the residue taken up in H$_2$O, and the mixture lyophilized. Purification of the residue by anion-exchange chromatography (Dowex 1×8 (HCOO$^-$): 0–0.7M HCOOH) [K. Wallimann, Helv. Chim. Acta 1990, 73, 1359] gave 17 which was immediately transformed into its Na-salt by anion-exchange chromatography (Dowex 50 W×4 (Na$^+$)).

Prodrug D was synthesized analogously as described in WO 92/19639.

Prodrug D:

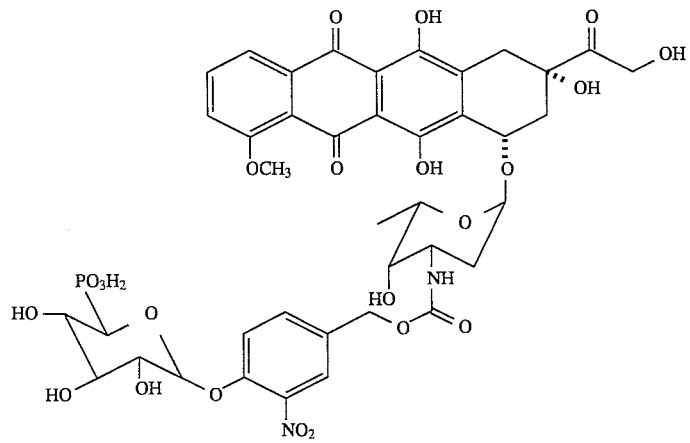

EXAMPLE 3

Comparison of Km- and V max-values of natural and improved substrate for antibody β-glucuronidase fusion protein For Km- and Vmax-determination 3'-N-[4-(beta-D-Glucuronyloxy)-3-nitro-benzyloxycarbonyl]-doxorubicin and prodrug A should be diluted in the range of 10–10000 μM in 100 mM phosphate buffer+1 mg/ml BSA, pH 7.2. Enzymatic cleavage should be done with constant amounts of fusion protein at 37° C. Cleavage can be monitored by HPLC analysis. Km- and Vmax-values can be calculated with the software program GraFit 2.0 (Erithacus Software Ltd.).

HPLC Analysis:

The HPLC apparatus consisted of an autosampler (Abimed, model 231), an automatic sample extraction system (AASP, Varian) equipped with minicartridges containing C 18 reversed phase silica gel (Analytichem), a gradient pump (Gynkotek, model 480), a fluorescence detector (Shimazdu RF 535, Excitation: 495 nm, Emission: 560 nm). Before sample injection the minicartridges were preconditioned with 2.5 ml methanol and 1.5 ml phosphate buffer, pH 6. Analytes retained on the reversed phase silica gel were then eluted by valve switching and connection of the minicartridges to the mobile phase. Chromatography was performed on reversed phase material (Nucleosil C 18, 5 μm particle size, 120 mm length, 4,5 mm I.D.) and gradient elution. Elution was done by a gradient composed of 2 components (A: 20 mM phosphate, pH 3, B: acetonitrile). The gradient was run with the following time-concentration profile:

| | |
|---|---|
| 0 min: | 75% A, 25% B |
| 20 min: | 25% A, 75% B |
| 30 min: | 25% A, 75% B |

Before starting the next run the column was allowed to equilibrate at starting conditions for 5 min.

| enzyme | substrate | Km mM | Vmax nmol/μg/min |
|---|---|---|---|
| antibody-β-glucuronidase fusion protein | 3'-N-[4-(beta-D-glucuronyloxy)-3-nitro-benzyloxycarbonyl]-doxorubicin (glucuronide prodrug) | 1.3 | 0.635 |
| | prodrug A (Km-reduced prodrug) | <0.5 | ~0.635 |

EXAMPLE 4

Prodrug A can be encapsulated according to D. Papahadjopoulos et al. (PNAS, U.S.A. 88:11460–11464, 1991) into stealth liposomes. After i.v. injection into CD1 nu/nu mice the plasma clearance of Prodrug A encapsulated into stealth liposomes should be prolonged from ≈20 min for the free Prodrug A to ≈40 hrs for the encapsulated Prodrug A. The significant t1/2β prolongation leads to improved pharmacological efficacy.

We claim:

1. A compound having the formula (I)

S—Z—W   (I)

wherein

S is an inhibitor of a human glycosidase and has the formula

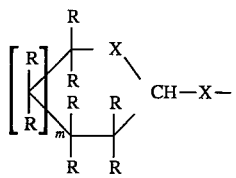

wherein each R is independently H, OH, F, $NH_2$, COOH, $CH_2$—COOH, CH(OH)—COOH, $PO_3H_2$, $CH_2$—$PO_3H_2$ or CH(OH)—$PO_3H_2$, X is NH, O or S, and m is 0 or 1;

W is a pharmacologically active substance; and

Z is a direct bond or a self-immolative spacer, provided that S is not β-D-glucuronic add or 2-amino-β-D-glucuronic acid when W is an anthracycline.

2. A compound according to claim 1, wherein

S has the formula

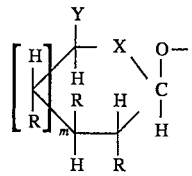

wherein

Y is COOH, $CH_2$—COOH, CH(OH)—COOH, $PO_3H_2$, $CH_2$—$PO_3H_2$ or CH(OH)—$PO_3H_2$, each R is independently H, OH, F or $NH_2$, X is NH, O or S, and m is 0 or 1;

W is a pharmaceutically active substance; and

Z is a direct bond or a self-immolative spacer having the formula

—A[—C(=A)—B—]$_p$—V(D)$_n$—B—C(=A)— wherein

V is an aromatic ring, a heteroaromatic ring, an alkenyl group having at least two conjugated double bonds or an amino acid residue that cyclizes after cleavage of the S—Z bond, each D is independently H, $CH_3$, $OCH_3$, COOH, $COOCH_3$, CN, OH, $NO_2$, F, Cl, Br, sulfonyl, sulfonamide or sulfon($C_1$–$C_4$)alkylamide, p is 0 or 1, n is an integer between 0 and 25, inclusive, A is O or NH, and B is O, NH, $CH_2O$, $CH_2NH$ or $CH_2$—N($C_1$–$C_4$-alkyl);

provided that S is not β-D-glucuronic acid or 2-amino-β-D-glucuronic add when W is an anthracyline.

3. A compound according to claim 1, wherein W is an anthracycline, an etoposide, N-bis-(2-chloroethyl)-4-hydroxyaniline, 4-hydroxycyclophosphamide, vindesine, vinblastine, vincristine, terfenadine, terbutaline, fenoterol, salbutamol, muscarine, oxyphenbutazone, salicylic acid, p-aminosalicylic add, 5-fluorouracil, 5-fluorocytidine, 5-fluorouridine, methotrexate, didofenac, flufenamicacid, 4-methylaminophenazone, theophylline, nifedipine, mitomycine C, mitoxantrone, camptothecine, m-AMSA taxol, nocodaxol, colchicine, cyclophosphamide, rachelmycin, cisplatin, melphalan, bleomycin, nitrogen mustard, phosphoramide mustard, quercetin, genistein, erbastatin, tyrphostin, rohitukine-derivative, retinoic acid, butyric acid, phorbol ester, DMSO, aclacinomycin, progesterone, buserelin, tamoxifen, mifepristone, onapristone, N-(4-aminobutyl)-5-chloro-2-naphthalenesulfonamide, pyridinyloxazol-2-one, quinolyloxazol-2-one, isoquinolyloxazol-2-one, staursporine, ethanolamine, verapamil, forskolin, 1,9-dideoxyforskolin, quinine, qunidine, resperine, 18-O-(3,5-dimethoxy-4-hydroxybenzyl)-reserpate, lonidamine, buthionine sulfoxamine, diethyldithiocarbamate, cyclosporine A, azathioprine, chlorambucil, N-(4-trifluoromethyl)-phenyl-2-cyano-3-hydroxy-croton-acid-amide, 15-deoxyspergualin, FK 506, ibuprofen, indomethacin, aspirin, sulfasalazine, penicillamine, chloroquine, dexamethasone, prednisolone, lidocaine, propafenone, procaine, mefonamic acid, paracetamol, 4-aminophenazone, muskosine, ociprenaline, isoprenaline, amiloride, p-nitrophenylguanidino-benzoate or a hydroxy-, amino- or imino-derivative thereof, linked through said hydroxy-, amino- or imino- group to Z.

4. A compound according to claim 2, wherein W is an anthracycline selected from the group consisting of doxorubicin, 4'-epi-doxorubicin, 4-desoxydoxorubicin and 4'-desoxydoxorubicin.

5. A compound according to claim 2, wherein V has from 5 to 20 carbon atoms and from 0 to 4 heteroatoms, wherein said heteroatom is O, N or S.

6. A compound according to claim 2, wherein n is 1 or 2.

7. A pharmaceutical composition comprising a compound according to claim 1 and a pharmaceutically acceptable carrier.

8. A pharmaceutical composition according to claim 7, wherein said pharmaceutically acceptable carrier is a liposome.

9. A pharmaceutical composition according to claim 7, further comprising a pretargeted enzyme, a catalytic antibody, an immunotoxin or an immunoconjugate.

* * * * *

UNITED STATES PATENT AND TRADEMARK OFFICE
CERTIFICATE OF CORRECTION

PATENT NO. : 5,621,002
DATED : April 15, 1997
INVENTOR(S) : Klaus BOSSLET et al.

It is certified that error appears in the above-indentified patent and that said Letters Patent is hereby corrected as shown below:

On the Title page, item [57], in the Abstract line 1, change "clearable" to --cleavable--.

Claim 2, column 12, line 46, change "add" to --acid--.

Claim 3, column 12, line 52, change "add" to --acid--;

Claim 3, column 12, line 53 change "didofenac" to --diclofenac--;

Claim 3, column 13, line 6, change "ociprenaline" to --orciprenaline--.

Signed and Sealed this

Twenty-first Day of October 1997

Attest:

BRUCE LEHMAN

*Attesting Officer*     *Commissioner of Patents and Trademarks*